(12) United States Patent
Moshe et al.

(10) Patent No.: US 6,228,071 B1
(45) Date of Patent: May 8, 2001

(54) DEVICES AND METHODS FOR CANNULATING A BLOOD VESSEL

(75) Inventors: Meir H. Moshe, El Sobrante; Jan Komtebedde, Cupertino; Robert K. Deckman, San Mateco, all of CA (US)

(73) Assignee: Heartport, Inc., Redwood City, CA (US)

( * ) Notice: Subject to any disclaimer, the term of this patent is extended or adjusted under 35 U.S.C. 154(b) by 0 days.

(21) Appl. No.: 09/293,592

(22) Filed: Apr. 16, 1999

(51) Int. Cl.$^7$ .................................................. A61M 31/00
(52) U.S. Cl. .............. 604/507; 604/164.04; 604/170.03; 604/174
(58) Field of Search .................. 604/164.01, 164.04, 604/174, 264, 170.03, 507, 523–528, 530, 532

(56) References Cited

U.S. PATENT DOCUMENTS

| | | | |
|---|---|---|---|
| 3,605,725 | * | 9/1971 | Bentov . |
| 5,498,251 | * | 3/1996 | Dalton ................................. 604/264 |
| 5,599,300 | * | 2/1997 | Weaver et al. ....................... 604/264 |

* cited by examiner

Primary Examiner—Anhtuan T. Nguyen
Assistant Examiner—Michael M. Thompson
(74) Attorney, Agent, or Firm—Jens E. Hoekendijk

(57) ABSTRACT

A cannula has a distal portion which is angled relative to a proximal portion. The distal portion is straightened during introduction with a stiffening element. After introduction, the stiffening element is removed so that the distal portion angulates relative to the proximal portion so that the cannula can be moved out of the surgical field. The cannula preferably includes a stabilizing ring having suture holders. The stabilizing ring is also preferably angled relative to the cannula.

9 Claims, 4 Drawing Sheets

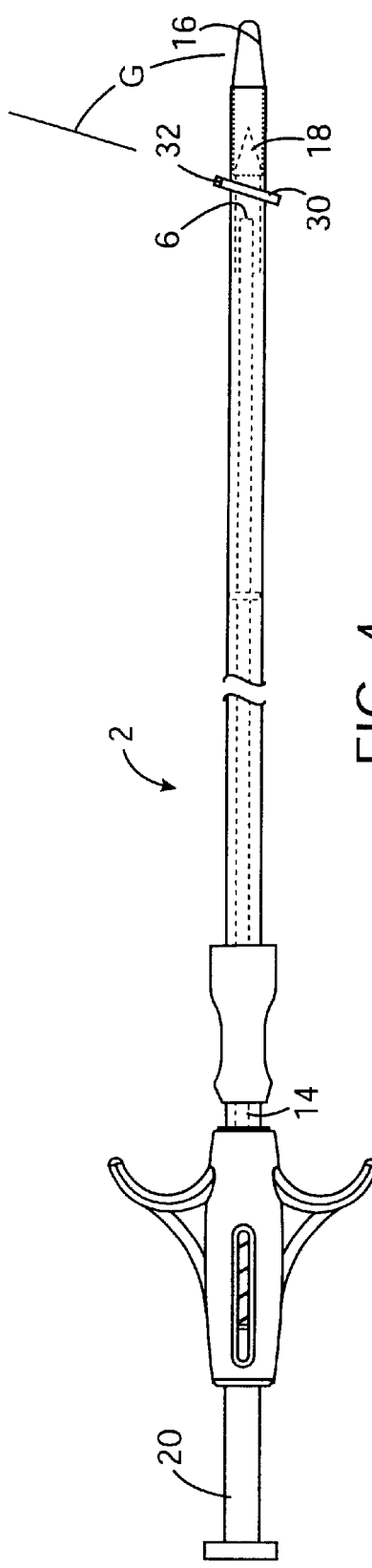
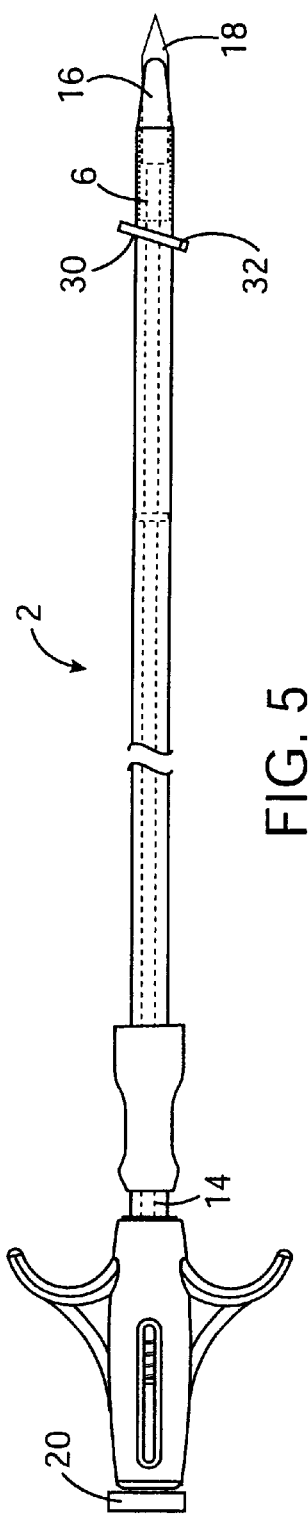
FIG. 4
FIG. 5

DEVICES AND METHODS FOR CANNULATING A BLOOD VESSEL

BACKGROUND OF THE INVENTION

The present invention relates to cannulae for introduction and withdrawal of fluids to and from a patient. A specific application of the present invention is for the return of oxygenated blood to the patient from a bypass system. The cannula of the present invention is particularly useful as an arterial cannula for cannulating the ascending aorta to return oxygenated blood to the patient for stopped-heart surgical procedures.

Conventional cannulae are generally long, flexible tubes which are draped over the patient when cannulating the ascending aorta. The cannulae can interfere with surgical procedures performed in the chest since the cannula cannot be bent enough to be moved completely out of the surgical field.

It is an object of the invention to provide improved methods and devices for cannulating a patient. In another object of the invention, improved methods and devices for cannulating the ascending aorta are provided.

SUMMARY OF THE INVENTION

The devices and methods of the present invention provide improved devices and methods for cannulating a patient. The cannula has a lumen and proximal and distal portions. The distal portion extends from the proximal portion and terminates at the distal end.

The proximal portion and distal portion are preferably angled relative to one another so that the proximal portion can be moved out of the surgical field and draped over the patient's chest. The distal portion may be angulated relative to the proximal portion in any manner such as a simple curve or bi-linear. The distal portion preferably forms an angle with the proximal portion of 60–150 degrees and the distal portion extends for about 25–35 mm.

When introducing the cannula into a vessel such as the ascending aorta, a stiffening element is introduced into the lumen to straighten the distal portion. After the cannula has been introduced into the patient, the stiffening element is removed permitting the distal portion to angulate relative to the proximal portion for moving the cannula out of the surgical field.

In another aspect of the invention, the stiffening element has an rounded tip which extends beyond the distal end of the cannula to facilitate introduction. The stiffening element also preferably includes an incising element for incising the vessel during introduction. The cannula may also have a stabilizing ring mounted to the distal portion. The stabilizing ring preferably has suture holders and forms an angle of 5–30 degrees with the cannula.

These and other advantages of the invention will become evident from the following description, drawings and claims.

BRIEF DESCRIPTION OF THE DRAWINGS

FIG. 4 shows the cannulae of FIGS. 1 and 2 with a stiffening element positioned therein to straighten a distal portion.

FIG. 5 shows the cannulae of FIG. 1 and 2 with an incising element exposed for incising a vessel.

DESCRIPTION OF THE PREFERRED EMBODIMENTS

Figure 1:
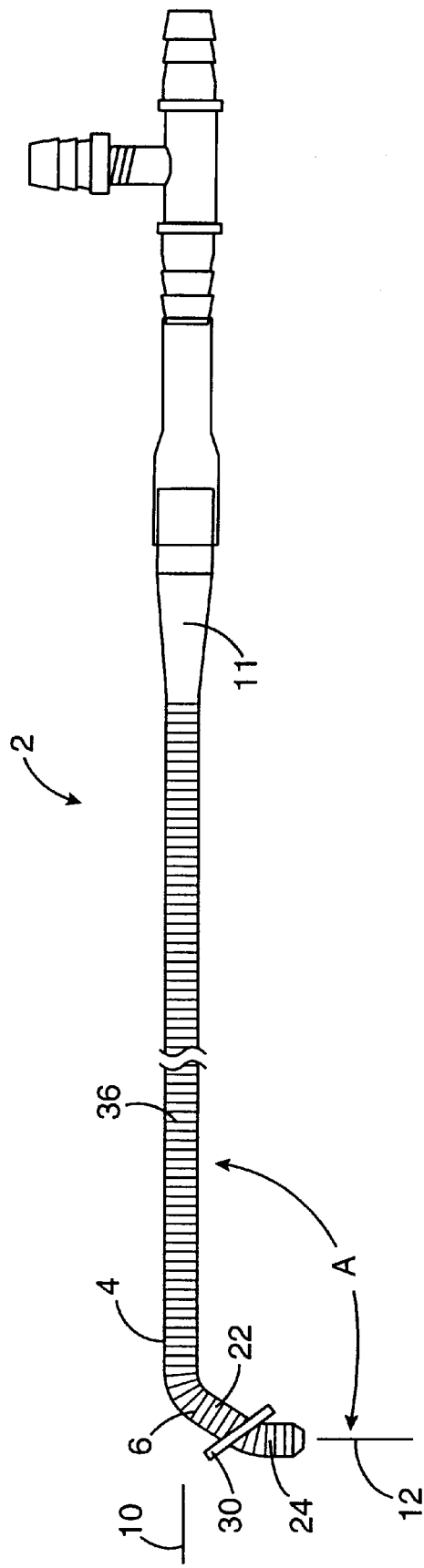
FIG. 1 shows a cannula in accordance with the present invention in an unbiased condition.

Referring to FIG. 1, a cannula 2 in accordance with the present invention is shown. The cannula 2 has a proximal portion 4 and a distal portion 6 which is angled relative to the proximal portion 4. As used herein, the various angles are relative to the central or longitudinal axis of the various parts of the cannula. For example, the proximal portion 4 has a central axis 10 and the distal portion has a central axis 12. The proximal portion 4 (or central axis 10) preferably forms an angle A of 70–130 degrees, more preferably 80–120 degrees and most preferably about 100 degrees with the distal portion 6 (or central axis 12). The distal portion 6 may have a bi-linear shape (FIG. 2) or a curved shape (FIG. 3).

Referring to FIGS. 4 and 5, the distal portion 6 is straightened with respect to the proximal portion 4 by a stiffening element 14. The stiffening element 14 has a smooth, rounded atraumatic tip 16 which facilitates introducing the cannula 2 into a blood vessel. The stiffening element 14 has an incising element 18 which is actuated by an actuator 20 to move the incising element from the retracted position of FIG. 4 to the exposed position of FIG. 5. The stiffening element 14 preferably reduces the angulation of the distal portion 6 to a relatively straight configuration, however, the straightening element 14 may also reduce the angulation without completely straightening the shaft. Furthermore, the stiffening element 14 may be malleable so that the angulation of the distal portion 6 is reduced but not to a completely straight configuration. The stiffening element 14 passes through lumen 11 which is preferably 18–24 French (FIG. 1).

Referring again to FIGS. 1 and 2, the distal portion 6 may have a bi-linear shape with a first section 22 and a second section 24. The first section 22 forms an angle B of about 25–65 degrees, preferably about 45 degrees, with the proximal portion 4. The second section 24 forms an angle C of about 100–140 degrees, preferably about 120, degrees, with the first section 22. The first section 22 extends for a length D of at least 15 mm and more preferably about 19 mm. The second section 24 extends for a length E of 5–15 mm, more preferably about 10–14 mm and most preferably about 12 mm. The overall length of the distal portion 6 is preferably about 20–40 mm, more preferably 25–35 mm and most preferably about 31 mm.

Figures 2, 3:
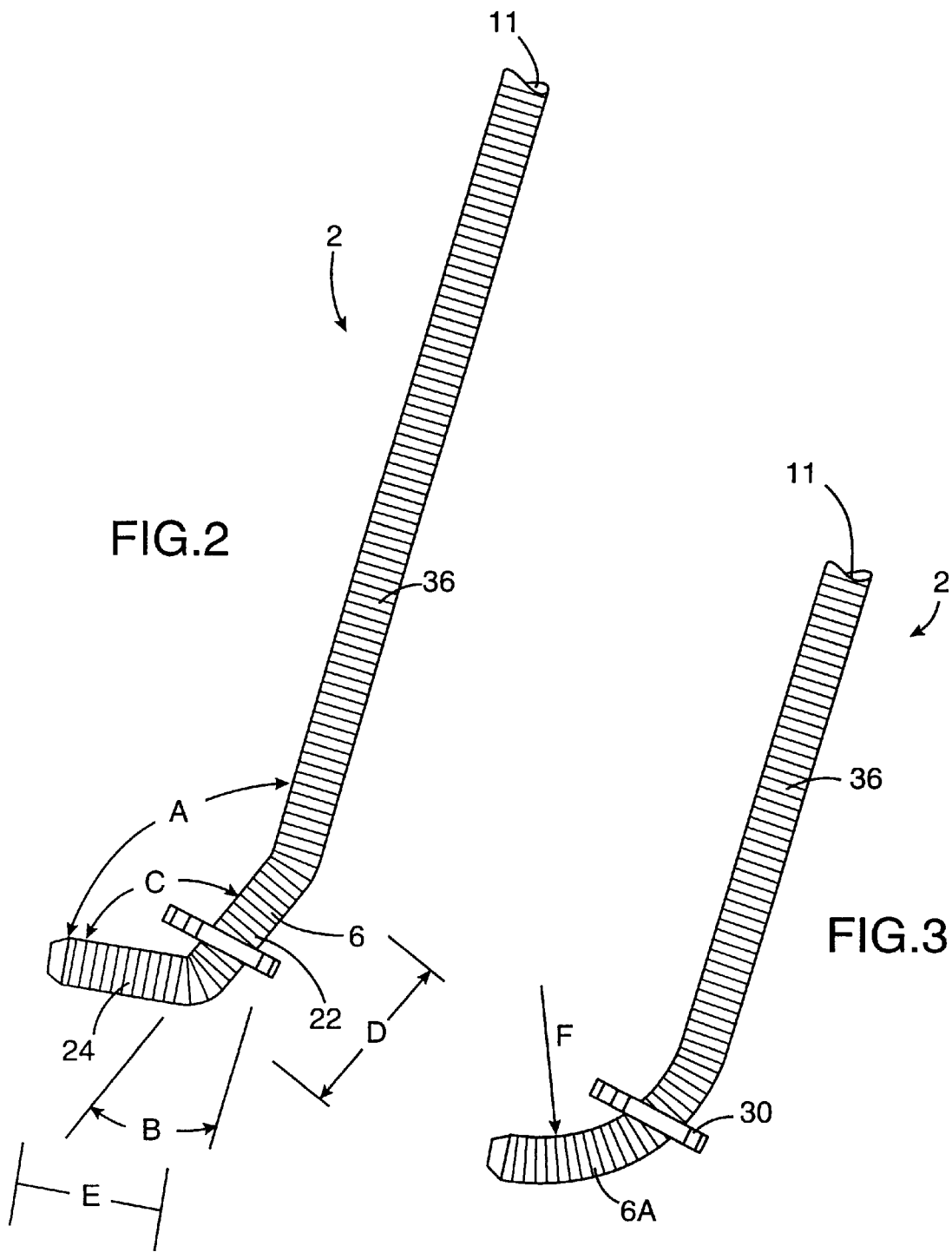
FIG. 2 is an enlarged view of the distal portion of the cannula of FIG. 1.
FIG. 3 is an enlarged view of another distal portion for the cannula of FIG. 1.

Referring to FIG. 3, another distal portion 6A is shown which has a curved shape with a radius of curvature F of about 6–32 mm, more preferably about 10–20 mm and most preferably about 16 mm. The length and angulation of the distal portion 6A for the curved embodiment of FIG. 3 is preferably the same as the distal portion 6 of FIG. 2 and additional dimensions may be calculated given the preferred angulation and configuration of the distal portion 6 described above.

The cannulae 2, 2A preferably include a stabilizing ring 30 which has at least one suture holder 32. The stabilizing ring 30 is mounted to the distal portion 6 and forms an angle G of 10–30 degrees and more preferably about 25 degrees.

Figure 6:
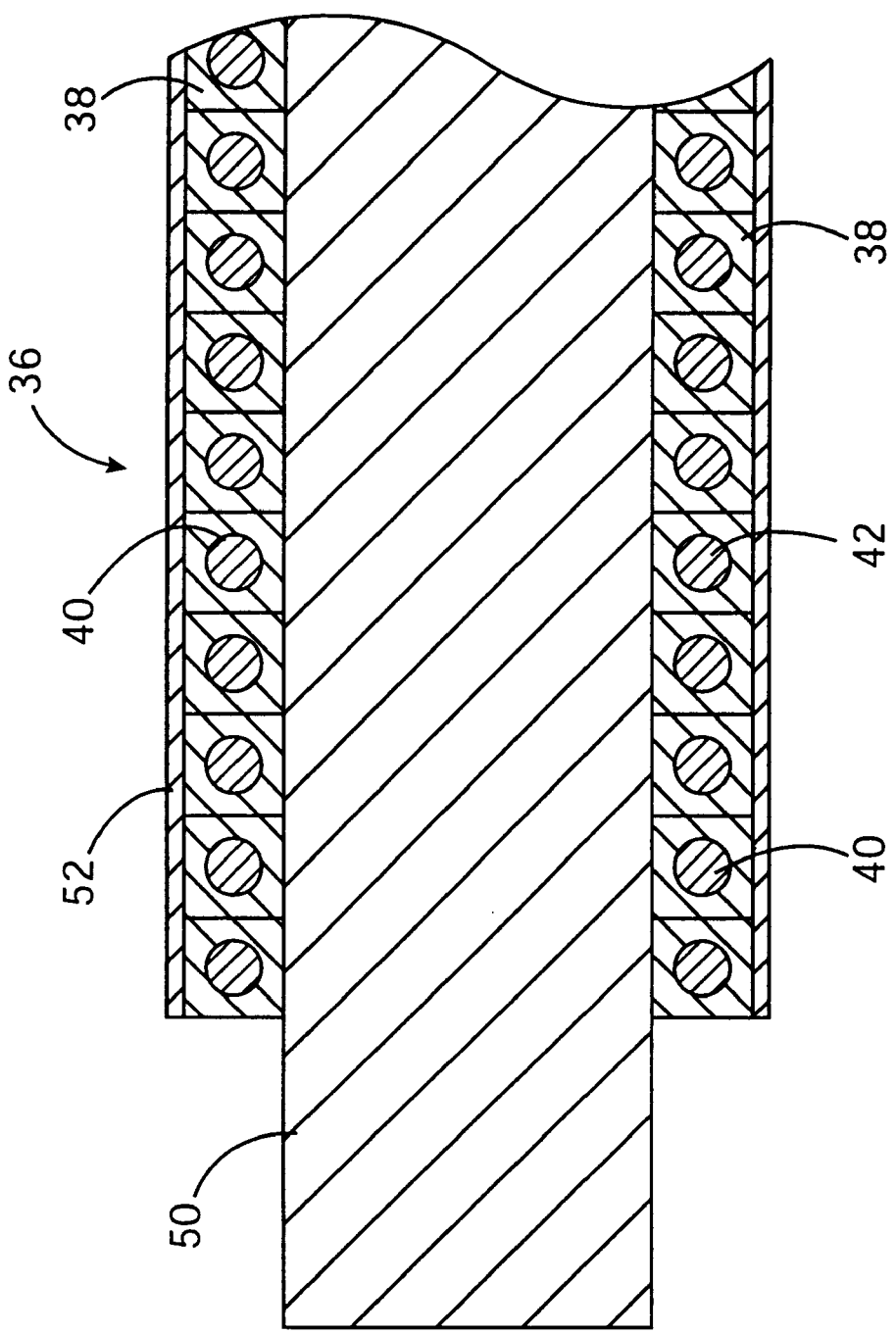
FIG. 6 is a cross-sectional view showing a method of constructing the shaft.

The cannula 2 may be formed in any suitable manner including a simple extrusion. The cannula preferably has wire reinforcing and is formed in the manner described in U.S. Pat. No. 5,863,366 which is incorporated herein by reference. Referring to FIG. 6, the shaft 36 is formed by extruding a material 38, preferably urethane, over an elongate member 40. The elongate member 40 is preferably a wire 42 having a diameter of 0.008 inches. The material 38 covers the elongate member 40 so that the extrusion has 0.014 inch sides forming a substantially square cross-section. The coated elongate member 40 is then wound onto a mandrel 50 in the manner shown in FIG. 6. A tube of material 52, preferably urethane having a thickness of 0.001 to 0.003 inch, is positioned over the coated elongate member 40. A shrink tube (not shown) is then positioned over the entire structure and the structure is heated to form an integrated structure as described in U.S. Pat. No. 5,863,366.

While the invention has been described with reference to the specific preferred embodiments, various alternatives and modifications may be used without departing from the scope of the invention. For example, the distal portion 6 may take any other suitable shape and the shaft may be a simple extruded tube.

What is claimed is:

1. A method of cannulating a patient, comprising the steps of;

providing a cannula having a lumen, a proximal portion, a distal portion extending from the proximal portion, a distal tip at the end of the distal portion, the distal portion being angled relative to the proximal portion in an unbiased condition, the cannula also having a stabilizing ring attached to the distal portion, the stabilizing ring forming an angle with the distal portion of about 10–30 degrees;

introducing a stiffening element into the lumen of the cannula, the stiffening element straightening the angle between the proximal and distal portions;

incising a blood vessel to create an incision;

passing the distal end of the cannula through the incision; and removing the stiffening element after the passing step so that the proximal and distal portions angulate relative to one another.

2. The method of claim 1, wherein:

the providing step is carried out with the distal portion having an axis which forms an angle of between 80–120 degrees with the proximal portion when in the unbiased position.

3. The method of claim 1, wherein:

the introducing step is carried out with the stiffening element having a tip which extends beyond the distal tip.

4. The method of claim 1, wherein:

the introducing step is carried out with a tip of the stiffening element being rounded and atraumatic.

5. The method of claim 1, wherein:

the introducing step is carried out with the stiffening element having an incising element positioned therein, the incising element being coupled to an actuator for moving the incising element from a retracted position to an exposed position, the incising element extending beyond the tip of the stiffening element in the exposed position; and the incising step is carried out with the incising element.

6. The method of claim 1, wherein:

the providing step is carried out with the lumen having a size of 18–24 French.

7. The method of claim 1, wherein:

the providing step is carried out with the distal portion having a curved shape.

8. The method of claim 1, wherein:

the providing step is carried out with the distal portion having a bi-linear shape.

9. The method of claim 1, wherein:

a providing step is carried out with the cannula having a stabilizing ring mounted to the distal portion, the distal portion extending 25–35 mm and the stabilizing ring being mounted 5–15 mm from the distal end.

\* \* \* \* \*